United States Patent
Lange et al.

(10) Patent No.: US 6,211,406 B1
(45) Date of Patent: Apr. 3, 2001

(54) PROCESS FOR THE MANUFACTURE OF α, α-BRANCHED CARBOXYLIC ACIDS

(75) Inventors: Jean-Paul Lange; Vincent Otten; Hans Arie Stil, all of Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/421,727

(22) Filed: Oct. 20, 1999

(30) Foreign Application Priority Data

Oct. 22, 1998 (EP) .................................................. 98203575

(51) Int. Cl.$^7$ ..................................................... C07C 51/14
(52) U.S. Cl. ............................................................. 562/521
(58) Field of Search ............................................... 562/521

(56) References Cited

U.S. PATENT DOCUMENTS 3,965,132   6/1976   Norell ........................... 260/410.9 R
5,342,979 * 8/1994   Mueller et al. .

FOREIGN PATENT DOCUMENTS

| 0249976 | 12/1987 | (EP) | C07C/53/128 |
| WO 92/18592 | 10/1992 | (WO) | C11D/1/28 |
| WO 96/20154 | 7/1996 | (WO) | C07C/51/14 |
| WO 97/38957 | 10/1997 | (WO) | C07C/2/06 |
| WO 98/38149 | 9/1998 | (WO) | C07C/51/14 |

* cited by examiner

*Primary Examiner*—Paul J. Killos
*Assistant Examiner*—John N Calve

(57) ABSTRACT

A process for manufacture of α,α-branched carboxylic acids from linear olefins by means of reaction with carbon monoxide and an acid catalyst, characterized in that a linear olefin containing from 2 to 5 carbon atoms, or a precursor thereof, is reacted in a batch reactor or a continuous reactor, with carbon monoxide and water, in the presence of a catalyst having sufficient acid groups to provide requisite protons for the formation of Koch acid, and in the presence of a polar non-coordinating organic solvent.

10 Claims, No Drawings

PROCESS FOR THE MANUFACTURE OF α, α-BRANCHED CARBOXYLIC ACIDS

The invention relates to a process for the manufacture of quaternary carboxylic acids. More in particular the invention relates to a process for the manufacture of α,α-branched carboxylic acids from linear olefins having from 2 to 5 carbon atoms by means of a Koch synthesis using carbon monoxide as reagent and a solid acid catalyst.

Processes for the preparation of α,α-branched carboxylic acids from branched olefins by means of a Koch synthesis, using carbon monoxide and water, are known.

International Application WO 96/20154 describes a process for the production of trialkylacetic acids from branched olefins and carbon monoxide in a non-aqueous reaction system using a solid resin catalyst comprising a cationic resin, having sufficient acid groups to provide requisite protons for conversion of branched olefin and carbon monoxide to trialkylacetic acids. In particular, the cationic resin was specified to have an acidity of at least equivalent to that of a 65 wt % sulphuric acid. It can be appreciated that such process can only be performed in two steps, i.e. one step comprising contacting the solid catalyst with olefin/CO feed and a subsequent step contacting the catalyst with water feed, and that stoichiometric amounts of branched olefin and water will not lead to the desired products in an acceptable yield. Moreover, such process cannot produce more than 1 mole of converted olefin per mole active proton on the solid catalyst in one cycle of two steps.

On the other hand, WO 92/18592 describes a process for the manufacture of trialkylacetic acids and particularly of pivalic acid, from branched olefins and particularly isobutene, and Carbon monoxide, using a solid acid catalyst together with minor amounts of a Lewis acid, such as boron trifluoride.

In addition, EP-A-0249976 describes a process for the manufacture of branched carboxylic acids, by catalytic conversion of olefins with carbon monoxide and water in the presence of zeolites as catalysts at temperatures of from 200 to 500° C. and at pressures of 200 to 700 bar. More in particular, zeolites of the pentasil type are used as catalysts. According to the exemplified embodiments only high temperatures (300° C.) and pressures (300–500 bar) are used. It can be appreciated that such reaction conditions will give rise to higher operation costs due to required measures as to safety and environment.

An object of the present invention is providing a further improved, efficient one step manufacturing process for α,α-branched carboxylic acids, which process starts from lower linear olefins containing from 2 to 5 carbon atoms, and which uses a catalyst system under relatively mild conditions on the one hand and which shows economically acceptable conversion and economically acceptable selectivity to α,α-branched carboxylic acids on the other hand.

As a result of extensive research and experimentation there has now been surprisingly found a one step process for manufacture of α,α-branched carboxylic acids from linear olefins by means of reaction with carbon monoxide and an acid catalyst, characterized in that a linear olefin containing from 2 to 5 carbon atoms, or a precursor thereof, is reacted in a batch reactor or a continuous reactor with carbon monoxide and water, in the presence of an acidic catalyst, having sufficient acid groups to provide requisite protons for the formation of Koch acids and in the presence of a polar non-coordinating organic solvent.

More in particular the invention relates to an improved manufacturing process of trialkylacetic acids of the formula

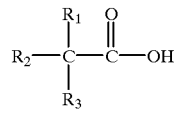

wherein each symbol R represents a radical having 1 to 10 carbon atoms.

More preferably the total number of carbon atoms in the trialkylacetic acids ranges from 5 to 11 and most preferably from 9 to 11 carbon atoms.

With the term "linear olefin or a precursor thereof" as used throughout the present specification is meant that the specified linear olefin itself as well as alcohols, esters or ethers, from which the specific olefin can be easily derived, can be used as starting materials for the present manufacturing process, which makes this process much more flexible than conventional prior art processes.

An important advantage of the present process is that it can be operated as one step or one reactor process showing an economically acceptable combination of conversion degree and selectivity and starting from cheap lower linear olefins which have been found to dimerize before the actual Koch synthesis step.

The catalyst to be used for the process of the present invention can be in general a strong acid catalyst which is known to efficiently catalyze the Koch synthesis, such as homogeneous $H_2O/BF_3$ catalyst, $H_2O/BF_3/H_3PO_4$ catalyst, or concentrated sulfuric acid or sulfonic acid catalysts, such as paratoluene sulfonic acid, methane sulfonic acid, trifluoromethane sulfonic acid, or a heterogeneous acidic solid catalyst. Homogeneous $H_2O/BF_3/H_3PO_4$ catalyst or methane sulfonic acid catalyst or a heterogeneous acidic catalyst are preferred.

More preferably a solid acidic ion exchanger showing strong acid behaviour is used. It is preferably selected from the group consisting of sulfonated resins and more preferably sulfonated copolymers of styrene and divinylbenzene, copolymers of vinylnaphthalene and divinylbenzene, copolymers of styrene and methacrylic acid resins, phenolic based resins, sulfonated poly(tetrafluoroethylene) and sulfonated siloxane polymers and sulfonated cellulose derivatives.

In either case of the presence of active sulfonic acid groups, the resin is treated to give a sulfonic acid cation-exchange resin capable of providing sufficient protons, i.e. the resin having an acid strength equivalent to at least 65 wt % sulphuric acid and preferably to at least 70 wt % sulphuric acid.

Catalyst solid resins, comprising sulfonic acid groups and derived from copolymers from styrene-divinylbenzene, copolymers from vinylnaphthalene-divinyl benzene or derived from (tetrafluoroethylene)polymers or from siloxane polymers are preferred.

Specific more preferred examples of commercial effective acidic catalysts are AMBERLYST, NAFION or DELOXAN catalysts (AMBERLYST, NAFION and DELOXAN are Trade Marks).

Most preferred are styrene-divinylbenzene copolymer based catalyst such as the AMBERLYST type catalysts. More preferably AMBERLYST 38 catalyst is used. The reaction temperature in the batch reactor is in the range of from 25° C. to 200° C. and preferably from 100 to 150° C.

The pressure in the reactor is in the range of from 1 to 200 bar and preferably from 50 to 100 bar.

As polar non-coordinating organic solvents can be used chemically inert polar organic solvents such as carboxylic acids or derivatives thereof and more in particular esters, or an optionally substituted sulfolane (preferably sulfolane).

According to a more preferred embodiment of the present process, as polar non-coordinating solvent an α,α-branched acid is present in the reactor and preferably a back mixed reactor. Most preferably the carboxylic acid to be produced can be used as solvent.

Normally the back mixed reactor is filled with solvent and catalyst with a catalyst/solvent wt ratio of in the range of from 0.01 to 0.5 w/w solid/liquid and preferably 0.2–0.3 w/w. The other respective reactants are introduced into the reactor and reaction mixture is heated to the desired 5–30 mmol/reaction temperature.

Alternatively for a fixed bed reactor with liquid recycling can be operated with a catalyst/solvent ratio up to 0.95 w/w (solid/liquid) and preferably in the range of from 0.4 to 0.8.

The feed of starting olefin is for batch processes in the range of from 0.3 to 2 mmol/g catalyst and preferably from 0.6 to 1.5 mmol/g catalyst and for continuous processes in the range from 0.1 to 10 mmol feed/gr cat/hr., while the water/olefin molar ratio or the molar ratio of the respective precursors therefor, is in the range of from 0.1 to 2 mole/mole and preferably about 0.5 and the CO/olefin molar ratio is in the range of from 0.5 to 1000 mole/mole and preferably from 1 to 100.

The invention is further illustrated by the following examples, however without restricting its scope to these specific embodiments.

EXAMPLE 1
With 1-Butene and Heterogeneous Catalyst

AMBERLYST 38 was dried overnight in an oven at 100° C. and a sample of 15 g dry AMBERLYST was loaded in a 250 ml autoclave together with 54 ml VERSATIC 11 acid, a branched $C_{11}$ carboxylic acid as solvent and 80 bar CO. The autoclave is then heated up to 150° C. under constant flow of 1.2 Nl/h (50 mmole/h) CO, 3.1 ml/h (33 mmole/h) 1-butene and 0.6 ml/h (33 mmole/h) water. After 17 h operation under these conditions the autoclave was cooled down to room temperature, depressurized and unloaded.

A sample of the product mixture was analyzed by means of gas chromatography. The carboxylic acids were extracted from the remaining fraction by means of washing with an equivalent volume of 4M NaOH solution, acidification of the NaOH extract to pH=1 with HCl, extraction of the carboxylic acids with an equivalent volume of diethyl ether and evaporation of the ether under mild heating. The concentrated carboxylic acid mixture was analyzed by means of gas chromatography.

The total product mixture contained some 67 C % carboxylic acids calculated as free from solvent. The extracted acid fraction contained 55 C % of Cg acids, corresponding to the dimer, with only 14 C % of CS acids, corresponding to the monomer, 20 C % C6–8 acid and 11 C % C10+acids, upon excluding the VERSATIC 11 acid used as solvent.

EXAMPLE 2
With Isoproyanol and Heterogeneous Catalyst

AMBERLYST 38 was dried overnight in an oven at 100° C. and a sample of 15 g dry AMBERLYST was loaded in a 250 ml autoclave together with 82 ml sulfolane solvent and 50 bar CO. The autoclave was then heated up to 150° C. under stationary CO gas cap and constant flow of 0.73 ml/h (9.5 mmol/h) isopropanol. After 65 h operation under these conditions the autoclave was cooled down to room temperature, depressurized and unloaded.

The reaction product was analyzed as described in ex. 1. The total product mixture contained some 12 C % carboxylic acids, the small amount being due to lack of sufficient amount of CO in this run. The extracted acid fraction contained 26 C % of $C_7$ acids, calculated as free from solvent, corresponding to the dimer, with 34 C % of $C_{5-6}$ acids and 49 C % of $C_{8+}$acid, upon excluding the sulfolane used as solvent.

EXAMPLE 3
With 1-Pentanol and Heterogenous Catalyst

AMBERLYST 38 was dried overnight in an oven at 100° C. and a sample of 15 g dry AMBERLYST was loaded in a 250 ml autoclave together with 66 ml sulfolane solvent and 50 bar CO. The autoclave was then heated up to 170° C. under stationary CO gas cap and constant flow of 2.3 ml/h (21 mmol/h) 1-pentanol. After 16 h operation under these conditions the autoclave was cooled down to room temperature, depressurized and unloaded.

The reaction product was analyzed as described in ex. 1. The total product mixture contained some 10 C % carboxylic acids calculated as free from solvent, the small amount being due to lack of sufficient amount of CO in this run. The extracted acid fraction contained 28 CO of $C_{11}$ acids, corresponding to the dimer, with 29 C % $C_6$ acid, corresponding to the monomer, 38 C % $C_{7-10}$ acids and 5 C % of $C_{12+}$ acid, upon excluding the sulfolane used as solvent.

EXAMPLE 4

In a similar way as described in example 1, carboxylic acids were prepared from ethanol, 2-propanol, and butene/water mixtures in molar ratios of 1:1 and 2:1 respectively.

In the experiments VERSATIC 11 Acid (VERSATIC is a trademark) has been used as solvent for the conversion of butene and water, ethanol and 2-propanol.

The relevant data have been listed in the following tables:

TABLE 1

| | Catalyst is Amberlyst 38; temp 150° C., 80 bar CO | | | | | | | |
|---|---|---|---|---|---|---|---|---|
| Feed | solvent | solvent (g) | feed rate (g/h) | catalyst (g) | CO-feed (l/h) | yield carboxylic acids [% C from olefin/alcohol] | Conversion [% C] | selectivity [% C] |
| 2-propanol | V11 | 49.82 | 0.816 | 15.22 | 1.35 | 17.85 | 94.47 | 18.90 |
| ethanol | V11 | 55.5 | 0.859 | 15.50 | 1.35 | 1.48 | 94.70 | 1.57 |
| 1-butene/-water 1:1 mole/-mole | V11 | 53.71 | 2.278* | 15.79 | 1.35 | 3.28 | 88.70 | 3.70 |

TABLE 1-continued

Catalyst is Amberlyst 38; temp 150° C., 80 bar CO

| Feed | sol-vent | sol-vent (g) | feed rate (g/h) | cata-lyst (g) | CO-feed (l/h) | yield carboxylic acids [% C from olefin/alcohol] | Conversion [% C] | selectivity [% C] |
|---|---|---|---|---|---|---|---|---|
| 1-butene/-water 2:1 mole/-mole | V11 | 53.93 | 3.640* | 15.50 | 1.90 | 40.72 | 95.02 | 42.85 |

*based on the total of 1-butene and water feed
+ respectively 1-butene and water

TABLE 2

GC results of washed product acids

| | Produced acids Normalized % | | | | | | | |
|---|---|---|---|---|---|---|---|---|
| Feed type | V4 | V5 | V6 | V7 | V8 | V9 | V10 | V11 |
| 2-propanol in V11 | 13.1 | 11.7 | 18.0 | 41.5 | 2.5 | 0.0 | 13.3 | 0.0 |
| ethanol in V11 | 0.0 | 68.2 | 31.8 | 0.0 | 0.0 | 0.0 | 0.0 | 0.0 |
| 1-butene water 1:1 mole/mole | 0.0 | 32.8 | 5.3 | 4.7 | 0.0 | 57.2 | 0.0 | 0.0 |
| 1-butene water 2:1 mole/mole | 0.0 | 23.0 | 5.3 | 4.0 | 4.0 | 63.7 | 0.0 | 0.0 |

EXAMPLE 5
With 1-Butene and Homogeneous Catalyst

To a 100 ml autoclave 30 ml (55 g.) of $BF_3/H_3PO_4/H_2O$ (molar ratio 1.5/1/1) catalyst and an extra amount of 6.3 g. $H_2O$ were added to obtain a water concentration of 18% w. The autoclave was heated to 80° C. and pressurized with 80 bar CO. Then 1-butene was pumped into the autoclave during a period of 30 minutes with a flow of 10 ml/hr. The reaction was allowed to proceed for another 30 minutes at constant temperature and pressure, fresh CO being supplied as required for keeping the pressure constant (80° C., 80 bar). Then the autoclave was cooled down to room temperature and depressurized. The autoclave content was poured into a separator funnel containing 50 g. ice. After vigorously shaking, the two liquid layers were allowed to separate and the water layer, containing residual $BF_3/H_3PO_4$ catalyst, was removed. The crude product layer was washed twice again with 25 ml of $H_2O$ collected, dried over anhydrous $MgSO_4$ and analyzed with GC using a 50 m capillary Free Fatty Acid Phase (FFAP) column with Helium as carrier gas. The product contained 40% w dimer acids ($C_9$ acid) and 30% w 2-methyl butyric acid (monomer acid).

COMPARATIVE EXAMPLE 1a
With Di-Isobutyl Carbinol and Heterogeneous Catalyst

AMBERLYST 38 was dried overnight in an oven at 100° C. and a sample of 4.4 g dry AMBERLYST was loaded in a 250 ml autoclave together with 28 ml pivalic acid solvent and 50 bar CO. The autoclave was then heated up to 150° C. under stationary CO gas cap and constant flow of 0.26 ml/h (1.5 mmol/h) DIBC and 0.26 ml/h (2.5 mmole/h) pivalic acid. The low feeding rate was chosen to ensure we have sufficient CO in the gas cap. After 17 h operation under these conditions the autoclave was cooled down to room temperature, depressurized and unloaded.

The reaction product was analyzed as described in ex. 1. The total product mixture contained some 73 C % carboxylic acids calculated as free from solvent. The extracted acid fraction contained 96 C % of $C_{10}$ acids, corresponding to the monomer, upon excluding the pivalic acid used as solvent.

COMPARATIVE EXAMPLE 2a
With 2-Octanol and Heterogenous Catalyst

AMBERLYST 38 was dried overnight in an oven at 100° C. and a sample of 15 g dry AMBERLYST was loaded in a 250 ml autoclave together with 78 ml sulfolane solvent and 50 bar CO. The autoclave was then heated up to 150° C. under stationary CO gas cap and constant flow of 3.8 ml/h (24 mmol/h) 2-octanol. After 17.5 h operation under these conditions the autoclave was cooled down to room temperature, depressurized and unloaded.

The reaction product was analyzed as described in ex. 1. The total product mixture contained some 11 C % carboxylic acids calculated as free from solvent, the small amount being due to lack of sufficient amount of CO in this run. The extracted acid fraction contained 93 C % of Cg acid, corresponding to the monomer, upon excluding the sulfolane used as solvent.

COMPARATIVE EXAMPLE 3a
With 1-Octene and Homogeneous Catalyst

To a 100 ml autoclave 50 ml (85 g.) $BF_3/H_3PO_4/H_2O$ (molar ratio 1.5/1/1) catalyst and an extra amount of 10.1 g. $H_2O$ were added to obtain a water concentration of 18% w. The autoclave was heated to 80° C. and pressurized with 80 bar CO. Then 1-octene was pumped into the autoclave during a period of 30 minutes with a flow of 10 ml/hr. The reaction was allowed to proceed for another 30 minutes at constant temperature and pressure (80° C., 80 bar). Than the autoclave was cooled down to room temperature and depressurized. The autoclave content was poured into a separator funnel containing 50 g. ice. After vigorously shaking, the two liquid layers were allowed to separate and the water layer, containing residual $BF_3/H_3PO_4$ catalyst, was removed. The crude product layer was washed twice again with 25 ml of $H_2O$, dried over anhydrous $MgSO_4$, collected and analyzed with GC using a 50 m capillary Free Fatty Acid Phase (FFAP) column with Helium as carrier gas. The product contained 51% w unconverted 1-octene and 46% w Cg acid (corresponding to the monomer).

We claim:
1. A process for manufacture of α,α-branched carboxylic acids from linear olefins comprising reacting the linear olefins with carbon monoxide in the presence of an acid catalyst, wherein the linear olefin, containing from 2 to 5 carbon atoms, or a precursor thereof, is dimerized and reacted in a batch reactor or continuous reactor with carbon monoxide and water, in the presence of a catalyst, having sufficient acid groups to provide requisite protons for the formation of Koch acid, and carbon monoxide into quater- nary carboxylic acids, and in the presence of a polar non-coordinating organic solvent.

2. The process of claim 1 wherein trialkylacetic acids of the formula

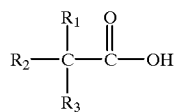

are produced, wherein each symbol R independently represents a radical having 1 to 10 carbon atoms.

3. The process of claim 1 wherein as the catalyst a homogeneous catalyst $H_2O/BF_3/H_3PO_4$ is used.

4. The process of claim 1 wherein as the catalyst a homogeneous catalyst trifluoromethane sulfonic acid is used.

5. The process of claim 1 wherein as catalyst a solid acidic ion exchanger, selected from the group consisting of sulfonated copolymers from vinylnaphthalene-divinylbenzene or styrene-divinyl benzene, sulfonated poly(tetrafluoroethylene) resins and sulfonated siloxane resins, is used.

6. The process of claim 5 wherein the resin is treated to give a sulfonic acid cation-exchange resin, such that the resin having an acid strength equivalent to at least 65 wt % sulphuric acid and preferably to at least 70 wt % sulphuric acid.

7. The process of claim 5 wherein the catalyst/solvent weight ratio is in the range of from 0.01 to 0.5 w/w for a suspension back mixed reactor.

8. The process of claim 5 wherein the catalyst/solvent weight ratio is in the range of from 0.4 to 0.8 w/w for a fixed reactor with liquid recycling.

9. The process of claim 1 wherein the water/olefin L molar ratio or the molar ratio of the respective precursor therefor is in the range of from 0.25 to 2 mole/mole.

10. The process of claim 1 wherein the CO/olefin molar ratio is in the range of from 0.25 to 1000 mole/mole.

* * * * *